US00PP30392P3

(12) United States Plant Patent
Wain

(10) Patent No.: US PP30,392 P3
(45) Date of Patent: Apr. 16, 2019

(54) ***CHRYSANTHEMUM* PLANT NAMED 'FICHRYBREPIN'**

(50) Latin Name: ***Chrysanthemum* X *morifolium***
Varietal Denomination: Fichrybrepin

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,511

(22) Filed: Nov. 21, 2017

(65) Prior Publication Data

US 2018/0146604 P1 May 24, 2018

Related U.S. Application Data

(60) Provisional application No. 62/497,574, filed on Nov. 22, 2016.

(51) Int. Cl.
*A01H 5/02* (2018.01)
*A01H 6/14* (2018.01)

(52) U.S. Cl.
USPC ..... Plt./297
CPC ..... *A01H 6/1424* (2018.05); *A01H 5/02* (2013.01)

(58) Field of Classification Search
USPC ..... Plt./286, 297
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Fichrybrepin', characterized by its upright to outwardly spreading and uniformly mounded plant habit; moderately vigorous growth habit; freely branching habit; dense and full plant form; uniform and freely flowering habit; large semi-decorative type inflorescences with light purple-colored ray florets; response time about 50 days under controlled photoperiodic treatments; and good postproduction longevity.

1 Drawing Sheet

Botanical designation: *Chrysanthemum* X *morifolium*.
Cultivar denomination: 'FICHRYBREPIN'.

BACKGROUND OF THE INVENTION

The present invention relates to a new and distinct *Chrysanthemum* plant, botanically known as *Chrysanthemum* X *morifolium*, commercially grown as a potted *Chrysanthemum* plant and hereinafter referred to by the name 'Fichrybrepin'.

The new *Chrysanthemum* plant is a product of a planned breeding program conducted by the Inventor in Fareham, Hampshire, United Kingdom. The objective of the breeding program is to create new potted *Chrysanthemum* plants with numerous attractive inflorescences.

The new *Chrysanthemum* plant originated from a cross-pollination made in January, 2013 by the Inventor in Fareham, Hampshire, United Kingdom of a proprietary selection of *Chrysanthemum* X *morifolium* identified as code number 85236, not patented, as the female, or seed, parent with a proprietary selection of *Chrysanthemum* X *morifolium* identified as code number 807589, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2013.

Asexual reproduction of the new *Chrysanthemum* plant by terminal vegetative cuttings was first conducted in Fareham, Hampshire, United Kingdom in December, 2013. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fichrybrepin'. These characteristics in combination distinguish 'Fichrybrepin' as a new and distinct *Chrysanthemum* plant:

1. Upright to outwardly spreading and uniformly mounded plant habit.
2. Moderately vigorous growth habit.
3. Freely branching habit; dense and full plant form.
4. Uniform and freely flowering habit.
5. Large semi-decorative type inflorescences with light purple-colored ray florets.
6. Response time about 50 days under controlled photoperiodic treatments.
7. Good postproduction longevity.

Plants of the new *Chrysanthemum* can be compared to plants of the female parent selection. Plants of the new *Chrysanthemum* differ primarily from plants of the female parent selection in ray floret color as plants of the female parent selection have inflorescences with yellow-colored ray florets.

Plants of the new *Chrysanthemum* can be compared to plants of the male parent selection. Plants of the new *Chrysanthemum* differ primarily from plants of the male parent selection in the following characteristics:

1. Plants of the new *Chrysanthemum* flower about three days later than plants of the male parent selection.
2. Plants of the new *Chrysanthemum* and the male parent selection differ in ray floret color as plants of the male parent selection have inflorescences with purple and white-colored ray florets.

Plants of the new *Chrysanthemum* can be compared to plants of *Chrysanthemum* X *morifolium* 'Breeze Rosy', not patented. In side-by-side comparisons, plants of the new *Chrysanthemum* differ primarily from plants of 'Breeze Rosy' in time to flower as plants of the new *Chrysanthemum* flower about two days later than plants of 'Breeze Rosy'. In addition, plants of the new *Chrysanthemum* and 'Breeze Rosy' differ in ray floret color as plants of 'Breeze Rosy' have inflorescences with pinkish white-colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a top perspective view of a typical flowering plant of 'Fichrybrepin' grown in a 14-cm container.

DETAILED BOTANICAL DESCRIPTION

The aforementioned photograph and following observations and measurements describe plants grown during the spring in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for about two weeks and then grown under short day/long night conditions to induce inflorescence initiation and development. Plants were nine weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Fichrybrepin'.

Parentage:

*Female, or seed, parent*.—Proprietary selection of *Chrysanthemum* X *morifolium* identified as code number 85236, not patented.

*Male, or pollen, parent*.—Proprietary selection of *Chrysanthemum* X *morifolium* identified as code number 807589, not patented.

Propagation:

*Type*.—Terminal vegetative cuttings.

*Time to initiate roots, summer*.—About ten days at temperatures about 21° C.

*Time to initiate roots, winter*.—About two weeks at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Medium in thickness, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous semi-decorative type potted *Chrysanthemum*; stems upright to outwardly spreading giving a uniformly mounded appearance to the plant; numerous lateral branches and relatively short internodes, dense and full plant form; moderately vigorous growth habit.

*Plant height*.—About 18 cm.

*Plant width*.—About 33 cm.

*Branching habit*.—Freely branching habit; about four primary lateral branches develop after removal of terminal apex (pinching).

*Lateral branches*.—Length: About 8 cm. Diameter: About 4 mm. Internode length: About 2 cm. Strength: Strong. Aspect: About 40° from vertical and then bending upwardly. Texture: Fine pubescence. Color: Close to 139C.

Leaf description:

*Arrangement*.—Alternate, simple.

*Length*.—About 7 cm.

*Width*.—About 5 cm.

*Shape*.—Palmately-lobed; roughly ovate with three to five lobes.

*Apex*.—Cuspidate.

*Base*.—Attenuate.

*Margin*.—Slightly dentate and palmately lobed; sinuses between lateral lobes mostly divergent.

*Texture, upper and lower surfaces*.—Fine pubescence; slightly rough; veins prominent on lower surface.

*Color*.—Developing leaves, upper surface: Close to N137B. Developing leaves, lower surface: Close to 137C. Fully expanded leaves, upper surface: Close to N137A; venation, close to 147D. Fully expanded leaves, lower surface: Close to 147B; venation, close to 147C.

*Petioles*.—Length: About 1.7 cm. Diameter: About 3 mm. Texture, upper and lower surfaces: Fine pubescence; slightly rough. Color, upper surface: Close to 147D. Color, lower surface: Close to 147C.

Inflorescence description:

*Form and flowering habit*.—Semi-decorative type inflorescence form with ligulate-shaped ray florets; inflorescences borne on terminals above and beyond the foliar plane; disc and ray florets arranged acropetally on a capitulum; freely flowering habit with about 35 inflorescences developing per plant during the flowering season.

*Fragrance*.—Mildly fragrant; pungent, herbaceous.

*Flowering response*.—Plants flower uniformly about 50 days after starting short day/long night photoperiodic treatments.

*Inflorescence longevity*.—Good postproduction longevity; inflorescences maintain good color and substance for about two to three weeks on the plant; inflorescences persistent.

*Inflorescence buds*.—Height: About 5 mm. Diameter: About 9 mm. Shape: Oblate. Color: Close to 137C.

*Inflorescence diameter*.—Large, about 9 cm.

*Inflorescence height*.—About 4 cm.

*Disc diameter*.—About 1.8 cm.

*Receptacles*.—Height: About 5 mm. Diameter: About 7 mm. Shape: Hemispherical. Color: Close to 145B.

*Ray florets*.—Number of ray florets per inflorescence: About 38 arranged in about four whorls. Orientation: Initially upright, then about 30° from vertical. Length: About 4 cm. Width: About 1.3 cm. Shape: Ligulate. Apex: Mammillate. Base: Fused into a short tube. Margin: Entire. Texture, upper and lower surfaces: Smooth, glabrous; double-keeled. Color: When opening, upper surface: Close to 70B. When opening, lower surface: Close to 75A. Fully opened, upper surface: Close to 77C; with development, color becoming closer to 75A. Fully opened, lower surface: Close to 76B; with development, color becoming closer to 76C.

*Disc florets*.—Number of disc florets per inflorescence: About 185 massed at the center of the receptacle. Length: About 6 mm. Diameter: About 1 mm. Shape: Tubular, elongated; apices, acute. Texture, inner and outer surfaces: Smooth, glabrous. Color, when opening: Apex: Close to 9A. Mid-section: Close to 1C. Base: Close to 157D. Color, fully opened: Apex: Close to 14A. Mid-section: Close to 1B. Base: Close to 157D.

*Phyllaries*.—Number of phyllaries per inflorescence: About 21 arranged in about three whorls. Length: About 7 mm. Width: About 2 mm. Shape: Lanceolate. Apex: Obtuse. Base: Obtuse. Margin: Entire. Texture, upper surface: Smooth, glabrous; waxy. Texture, lower surface: Fine pubescence; waxy. Color, upper surface: Close to 143A. Color, lower surface: Close to 137C.

*Peduncles*.—Length, terminal peduncle: About 2 cm. Diameter, terminal peduncle: About 3 mm. Angle: Erect to about 20° from vertical. Strength: Moderately strong. Texture: Densely pubescent. Color: Close to 137C.

*Reproductive organs*.—Androecium: None observed. Gynoecium: Present only on ray florets. Pistil length: About 6 mm. Stigma shape: Bi-parted. Stigma color: Close to 5A. Style length: About 4 mm. Style color: Close to 145D. Ovary color: Close to 1D.

*Seeds and fruits*.—Seed and fruit production has not been observed on plants of the new *Chrysanthemum* to date.

Disease & pest resistance: Resistance to pathogens and pests common to *Chrysanthemum* plants has not been observed on plants of the new *Chrysanthemum* to date.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fichrybrepin' as illustrated and described.

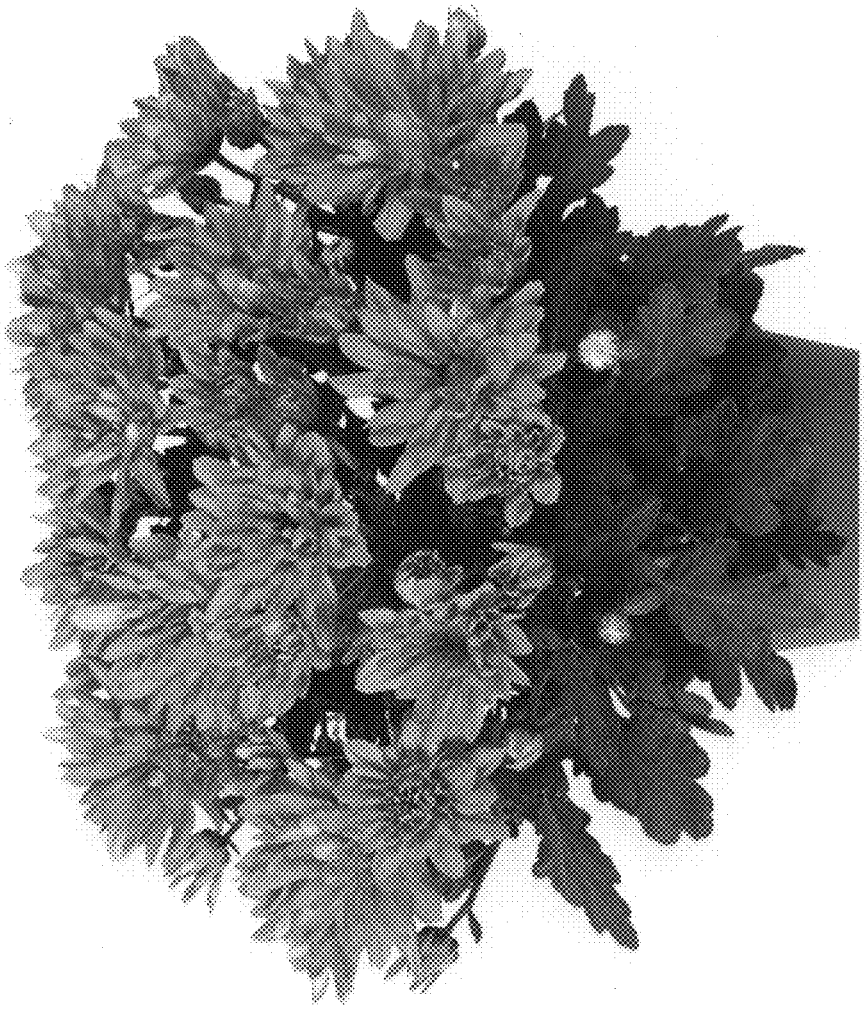

* * * * *